(12) United States Patent
Sobue et al.

(10) Patent No.: US 7,808,246 B2
(45) Date of Patent: Oct. 5, 2010

(54) APPARATUS AND METHOD FOR VERIFYING A SEAL BETWEEN MULTIPLE CHAMBERS

(75) Inventors: Katsuyoshi Sobue, Tokyo (JP); Takeshi Nakajima, Tokyo (JP); Atsushi Matsuzaki, Tokyo (JP); Minoru Okuda, Tokyo (JP)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 173 days.

(21) Appl. No.: 11/773,501

(22) Filed: Jul. 5, 2007

(65) Prior Publication Data

US 2009/0009179 A1 Jan. 8, 2009

(51) Int. Cl.
G01R 31/00 (2006.01)
G01R 31/08 (2006.01)
(52) U.S. Cl. .................... 324/519; 324/500; 324/515
(58) Field of Classification Search .............. 324/519, 324/500, 515
See application file for complete search history.

(56) References Cited

U.S. PATENT DOCUMENTS

| | | | |
|---|---|---|---|
| 4,055,252 A | 10/1977 | Klamm et al. | |
| 4,182,451 A | 1/1980 | Watson | |
| 4,688,891 A | 8/1987 | Carratt et al. | |
| 4,703,314 A | 10/1987 | Spani | |
| 4,735,240 A | 4/1988 | Ziegler | |
| 4,744,395 A | 5/1988 | Ziegler | |
| 4,779,460 A | 10/1988 | Cruickshank | |
| 4,801,926 A | 1/1989 | Bitetti | |
| 4,917,155 A | 4/1990 | Koblasz et al. | |
| 4,958,518 A | 9/1990 | Duenstl et al. | |
| 5,111,184 A * | 5/1992 | Heaton et al. | 340/542 |
| 5,230,439 A | 7/1993 | Klok et al. | |
| 5,257,985 A * | 11/1993 | Puhl | 604/410 |
| 5,524,486 A | 6/1996 | Hermann | |
| 5,533,392 A * | 7/1996 | Kira | 73/290 B |
| 5,894,089 A | 4/1999 | Ogawa | |
| 6,106,612 A | 8/2000 | White | |
| 6,121,555 A | 9/2000 | Nowosielski et al. | |
| 6,202,487 B1 | 3/2001 | Urias et al. | |
| 6,219,933 B1 | 4/2001 | Taniguchi et al. | |
| 6,312,074 B1 | 11/2001 | Walker | |
| 6,370,951 B1 | 4/2002 | Kerchaert et al. | |
| 6,397,674 B1 | 6/2002 | Kerchaert et al. | |
| 6,472,887 B1 * | 10/2002 | Tullis et al. | 324/663 |
| 6,526,824 B2 | 3/2003 | Chase et al. | |
| 6,536,861 B1 | 3/2003 | Usui et al. | |
| 6,622,557 B2 | 9/2003 | Petzold | |
| 6,663,743 B1 * | 12/2003 | Becker et al. | 156/273.7 |
| 6,736,006 B2 | 5/2004 | Arias | |
| 6,799,820 B1 | 10/2004 | Usui et al. | |

(Continued)

*Primary Examiner*—Timothy J Dole
*Assistant Examiner*—Farhana Hoque
(74) *Attorney, Agent, or Firm*—K&L Gates LLP

(57) ABSTRACT

An open seal check system for a multi-chamber supply container having at least one elongated seal, the system includes: (i) a base configured to support the multi chamber container; (ii) a plurality of electrodes positioned on the base so as to be at least substantially parallel with the elongated seal; and (iii) electronics connected to the electrodes, the electrodes each forming a capacitor with the multi-chamber supply container when the container is placed on the base, the electronics configured to output a single indication of a dielectric associated with each capacitor.

18 Claims, 13 Drawing Sheets

U.S. PATENT DOCUMENTS

| | | |
|---|---|---|
| 6,869,158 B2 | 3/2005 | Kojima et al. |
| 6,952,963 B2 | 10/2005 | Delnevo |
| 7,013,727 B2 | 3/2006 | Delnevo |
| 7,055,926 B2 | 6/2006 | Kojima et al. |
| 7,157,727 B2 | 1/2007 | Kimura |
| 7,175,244 B2 | 2/2007 | Usui et al. |
| 7,188,520 B2 | 3/2007 | Usui et al. |
| 7,206,715 B2 | 4/2007 | Vanderveen et al. |
| 7,243,893 B2 * | 7/2007 | Sobue et al. ................ 248/459 |
| 7,267,000 B1 | 9/2007 | Usui et al. |
| 7,270,386 B2 | 9/2007 | Takahashi et al. |
| 7,304,583 B2 | 12/2007 | Beller |
| 2004/0241041 A1 * | 12/2004 | Woodworth et al. .......... 422/22 |
| 2005/0131332 A1 * | 6/2005 | Kelly et al. ................ 604/4.01 |
| 2005/0133674 A1 * | 6/2005 | Sobue et al. ................ 248/95 |

* cited by examiner

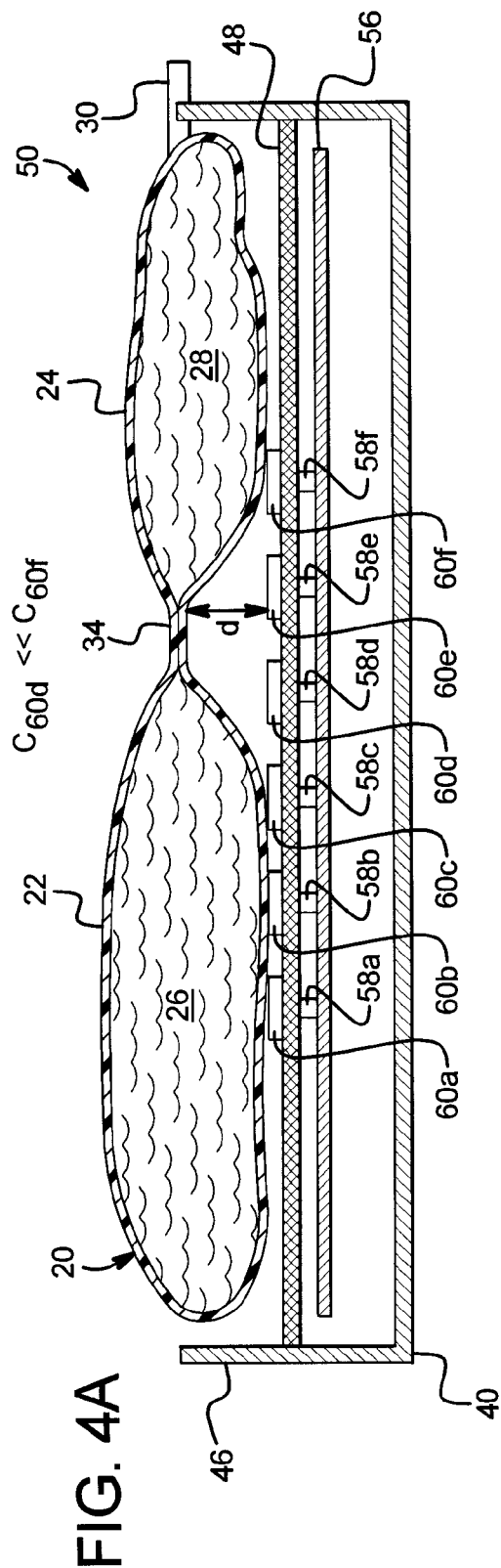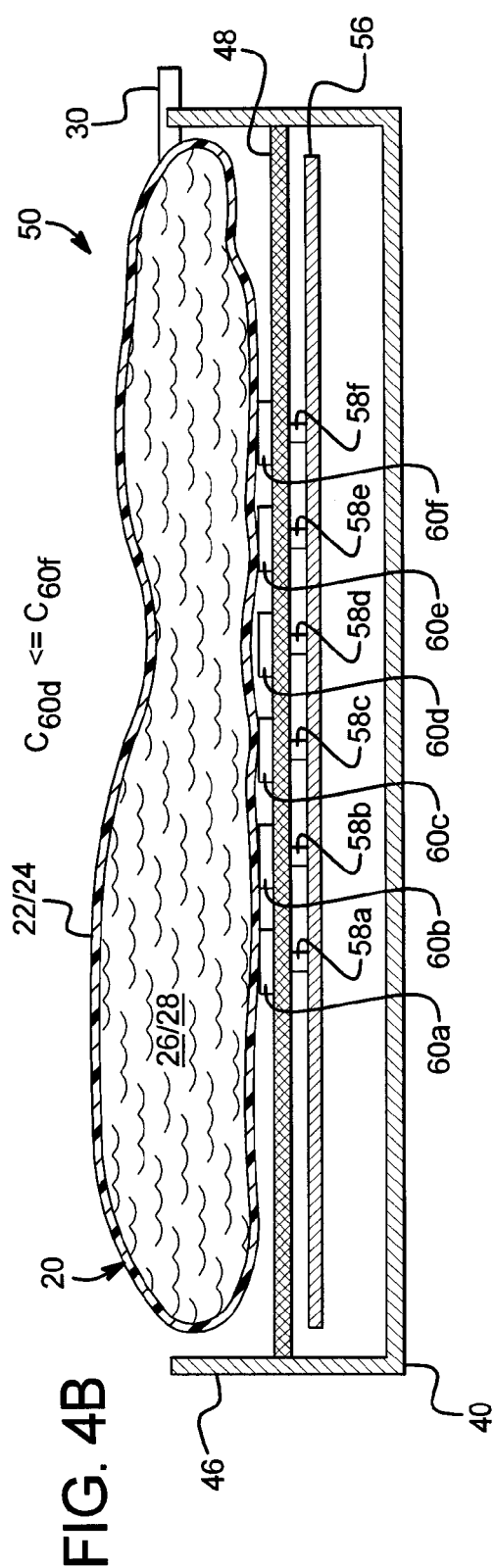
FIG. 4A
FIG. 4B

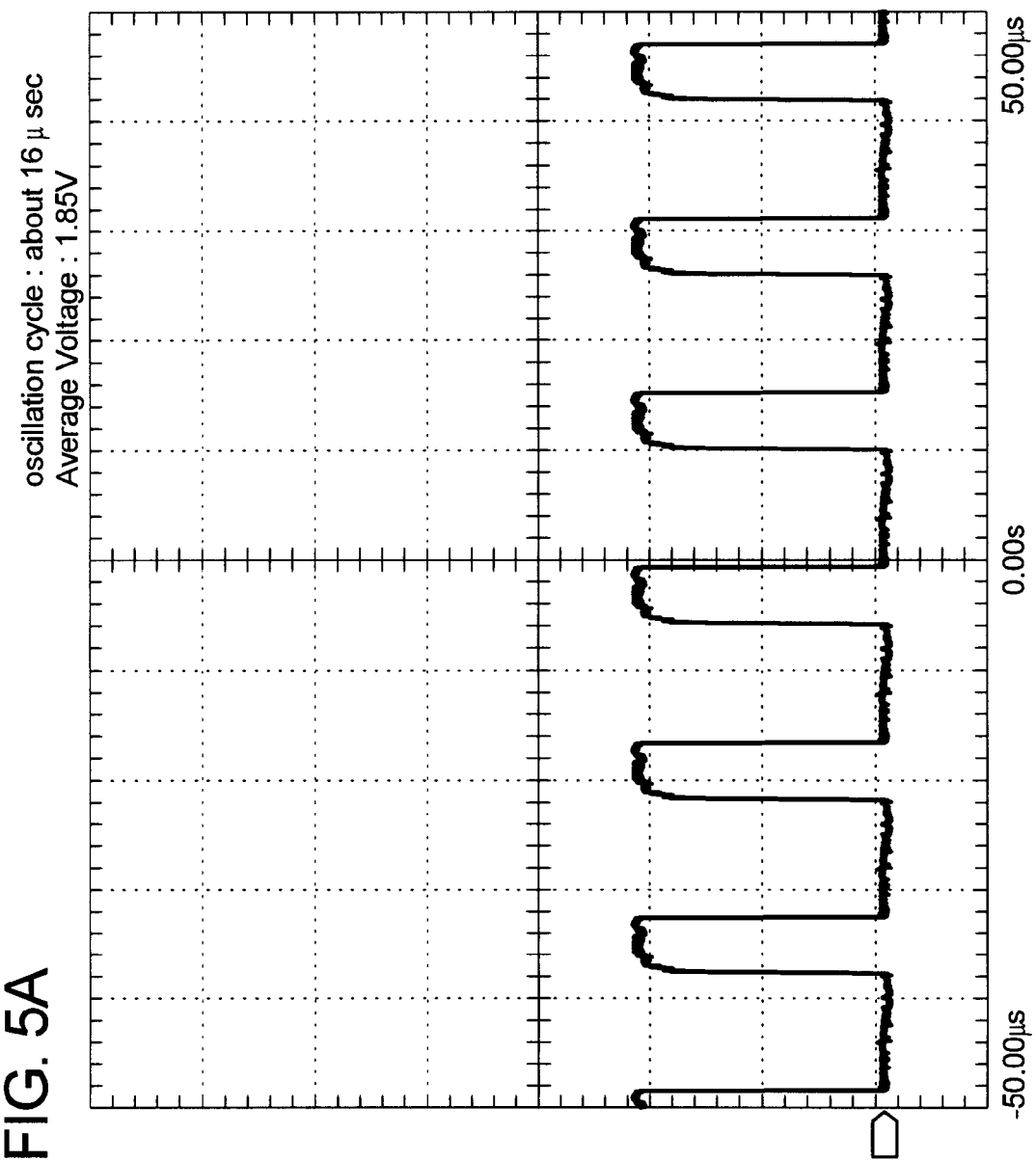

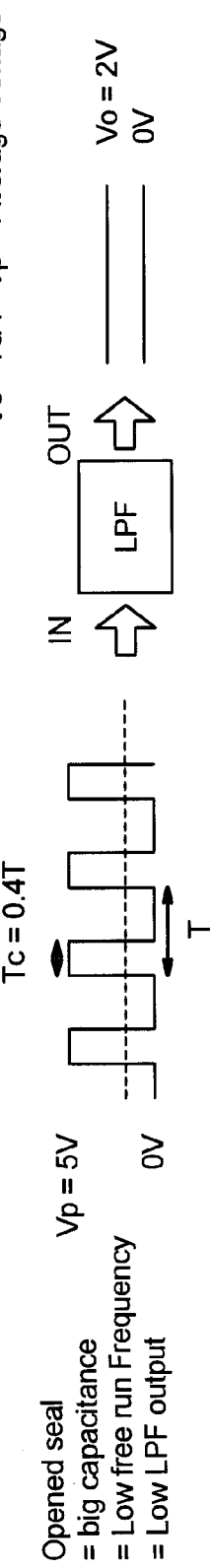

FIG. 5C

2nd rectangular wave

Tc = 0.8T

Closed seal
= small capacitance
= High free run Frequency
= High LPF output

Vp = 5V
0V

Low Pass Filter (LPF) Output = Vo

Vo = 4V
0V $Vo = Tc/T \cdot Vp$ = Average Voltage

Tc = 0.4T

Opened seal
= big capacitance
= Low free run Frequency
= Low LPF output

Vp = 5V
0V

Vo = 2V
0V

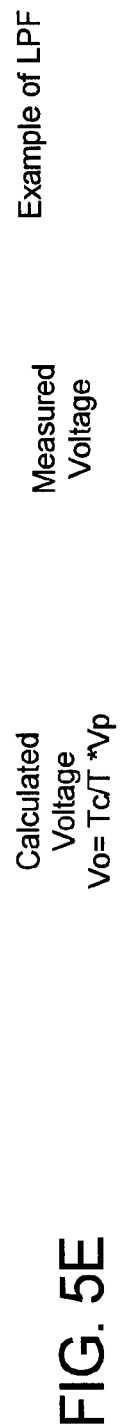

FIG. 5D

Example of LPF

| | Tc(μs) | Tc(μs) | Vp | Calculated Voltage $Vo = Tc/T \cdot Vp$ | Measured Voltage | |
|---|---|---|---|---|---|---|
| FIG. 5A | 6.4 | 16 | 4.5 | 1.8 | 1.85 | Closed Seal |
| FIG. 5B | 6.4 | 19 | 4.5 | 1.515789 | 1.5 | Opened Seal |

FIG. 5E

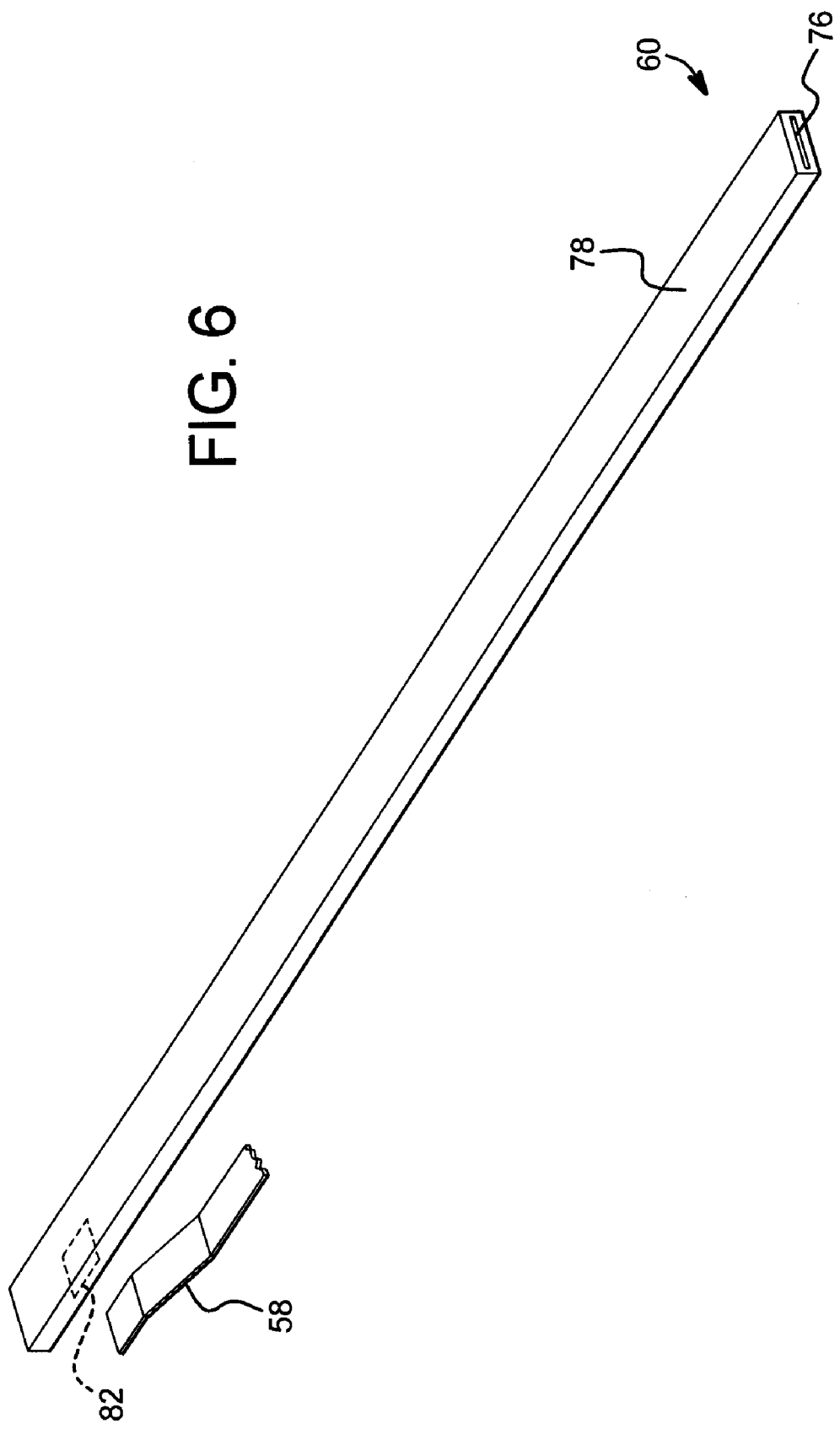

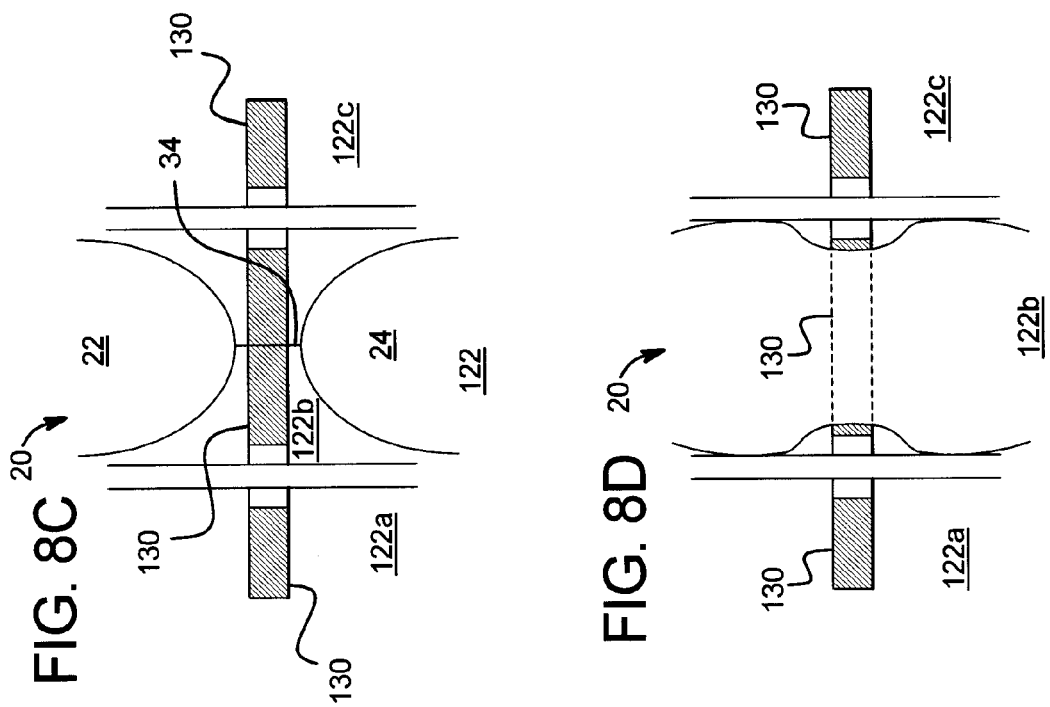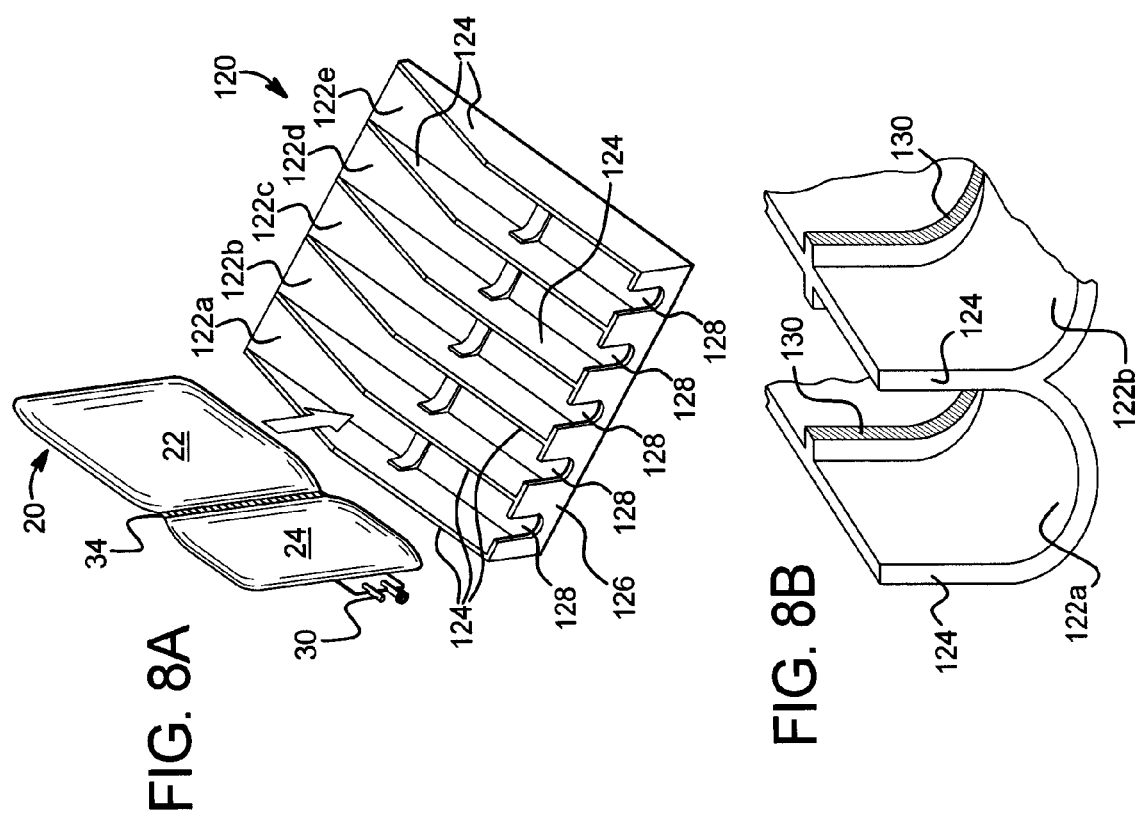

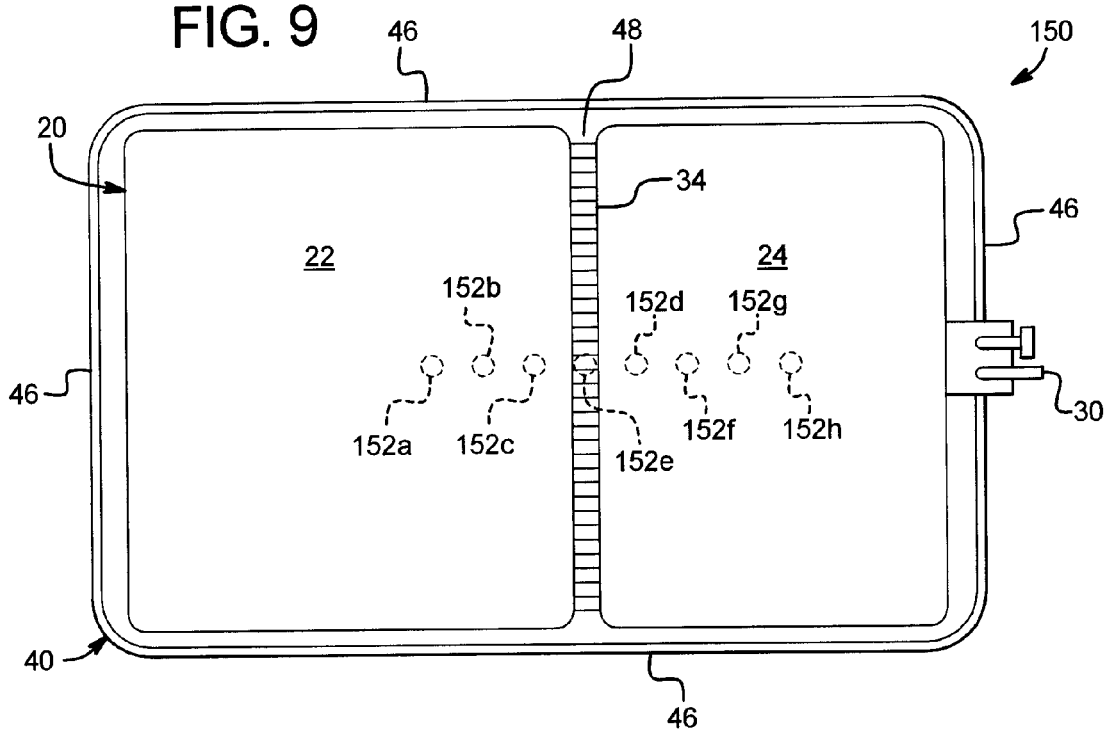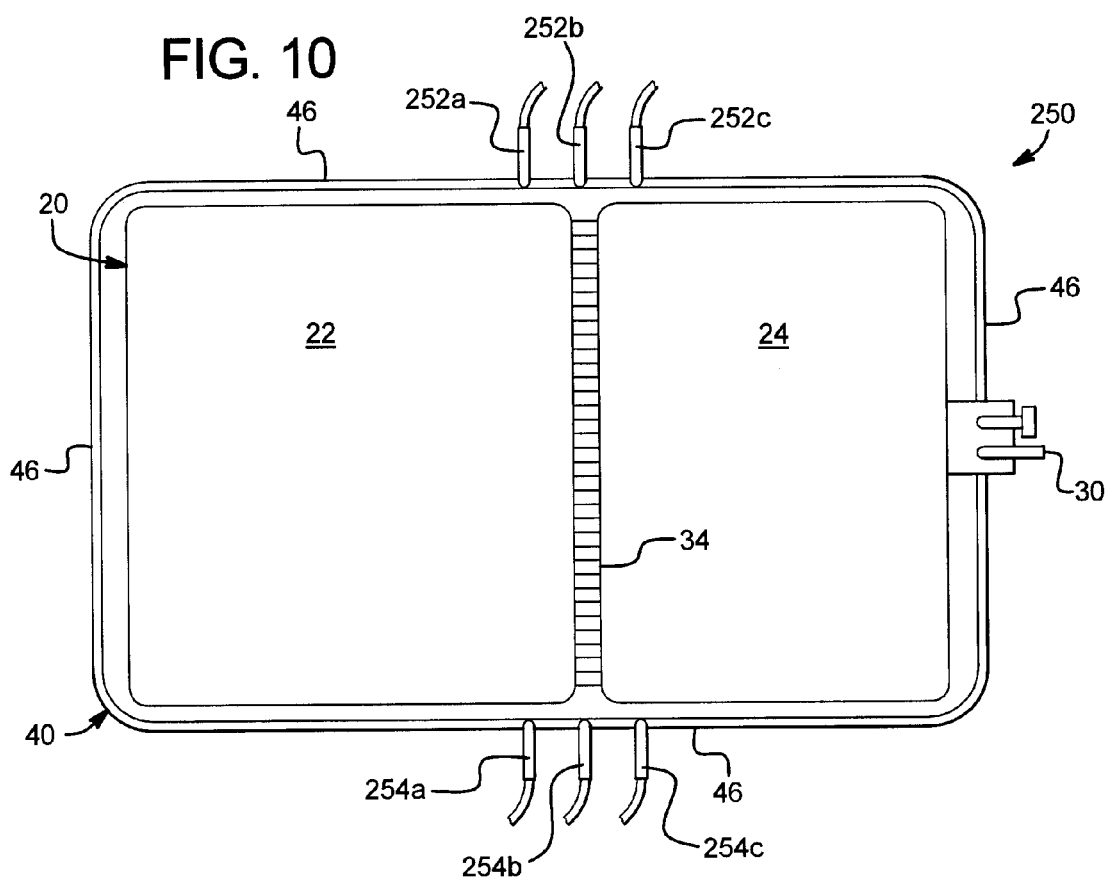

APPARATUS AND METHOD FOR VERIFYING A SEAL BETWEEN MULTIPLE CHAMBERS

BACKGROUND

The present disclosure relates to the detection of multi-chambered fluid structures, and in particular, to an apparatus for verifying that a seal between a multi-chambered structure has been opened properly for therapy.

Multi-chambered structures in which adjacent chambers are separated by a seal are known. Examples of multi-chambered structures include a two-chamber bag containing liquids to be mixed. Multi-chamber structures are particularly useful in the medical field in which different medications are to be combined at the bedside of a patient or point of use. The multiple chambers allow the medications to be separated by a seal until the appropriate time at which the seal is broken and the medications are mixed.

The seal between the chambers of the multi-chamber structure may be releasable, but the integrity of the seal should be selectively maintained. Multi-chambered structures are typically produced by a plastic sheet that is passed through a heat sealing mechanism that provides a seal to separate adjacent chambers. The rapidity in which the heat sealing is performed varies by application. Multi-chambered structures can also be produced by opposing sheets of material being fed into a mold that produces a shaped structure having separated chambers. The seal between chambers provides a barrier, thereby preventing the contents of one chamber from mixing with the adjacent chamber or preventing adjacent chambers from becoming a large, single chamber. During production, verification of the integrity of the seal is performed for example by visual inspection.

Various medical treatments, such as peritoneal dialysis, use dual bag solutions. Peritoneal dialysis solution is called dialysate. Dialysate has traditionally included lactate in a single chamber bag. More recently, dialysate has been made to be bicarbonate based. Bicarbonate is unstable in the presence of magnesium and calcium and forms a precipitate after a period of time. Accordingly, bicarbonate based dialysate needs to be packaged in a dual chamber supply container or bag.

The two chambers of the dual chamber bag are separated by a seal that a person breaks without tearing the entire bag. One such seal provided by the assignee of the present disclosure is termed a peel seal. Premature mixing of the contents of adjacent chambers may have deleterious effects on the resulting combination or render the combination of contents useless after an extended time. Accordingly, just prior to use, the patient or caregiver breaks the seal between the two chambers and the solution from the two chambers is mixed and used before a calcium or magnesium precipitate can form.

The two unmixed solutions separated by the peel seal pose a risk. Each solution taken individually can be physiologically unsafe for the patient. Accordingly, it is necessary to properly mix the individual solutions to form the final solution before injecting any of the solutions into the patient or contacting any of the solutions with the patient's blood. Allowing one of the solutions alone to reach the patient presents a potentially physiologically unsafe condition.

Accordingly, a reliable system for detecting whether or not a dual chamber solution bag has been opened is needed.

SUMMARY

The present disclosure provides a system and method for determining whether a dual or multi-chamber medical fluid bag has been opened prior to its use to ensure that the separated fluids have been allowed to mix before patient infusion. The system and method are particularly well-suited for peritoneal dialysis ("PD"), however, the present disclosure is not limited to PD and applies instead to any medical fluid procedure employing a dual or multi-chamber supply container or bag.

In the context of PD, in one embodiment the system and method operate with a PD dialysate heater. The heater can be used with manual or continuous ambulatory PD ("CAPD") or be integrated with an automated peritoneal dialysis ("APD") machine. The heater heats the dialysate from its stored temperature to a body temperature (e.g., 37° C.).

The dual or multi-chamber bag is placed on the heater to warm the fluid therein to the desired temperature. Because the bag needs to be placed on the heater for a period of time, the heater provides an opportune place to check if the dual chamber bag is open or not. In an alternative embodiment however, the open seal check system and method are not used with a heater and are provided instead with a mat or base that holds the supply bag.

As described in detail herein, in one embodiment the heater is fitted with thin, insulated electrode strips. The strips are placed in parallel to one another. The conductive, e.g., metallic, electrodes form one plate of a capacitor. The relatively conductive fluid within the dual chamber bag forms the other plate of the capacitor. The relatively non-conductive film of the bag, the insulation on the electrodes and an air gap (potentially at the seal area) between the electrodes and the medical fluid forms a dielectric between the capacitor plates. In this manner, each electrode forms a separate capacitor, which is in parallel with each other electrode.

The multi-chamber bag when closed and laid on its side forms a discontinuous profile. That is, the bag pinches together along the seal that separates two chambers. The bag material in the middle of the fluid chambers contacts the heater and the insulated electrodes. The bag material at and near the seal is raised off of the heater and corresponding electrode, creating an air pocket between the multi-chamber bag and the electrodes. The air pocket provides for a different dielectric constant at the seal than does the combination of bag filter and electrode insulation at the middle of fluid chambers. The different dielectric constant results in a different measurable electrical output (e.g., average voltage due to changing electrode capacitance and frequency due to changing equivalent capacitance). The different measurable electric output enables an unopened bag to be detected.

It should be appreciated from the above-description that the multi-chamber bag should be placed on the heater such that the seal (opened or closed) is aligned with or parallel with the electrodes as much as possible. It is also desirable that the seal (opened or closed) be placed directly above one of the electrodes, such that the particular electrode is in an optimum position to sense different dielectrics due to the presence or absence of an air pocket from the presence or absence of the closed seal. In one embodiment therefore, the heater includes alignment an apparatus to align and orient the bag properly.

The electrodes and each connected to electronics that enable the dielectric constant associated with each electrode to be correlated to a measurable electrical output. In one embodiment each electrode is connected to an astable multi-vibrator. The astable multi-vibrator applies a voltage to each electrode (e.g., in a sequence using a multiplexer) and records a corresponding output average voltage and frequency for each electrode (for each capacitor plate or electrode). The outputted average voltage and frequency are different at a sealed portion of the bag versus that for the middle of a chamber and versus that for the same area of the bag when unsealed. The outputted frequency (based on equivalent capacitance as described below) is higher and the outputted average voltage is more (based on electrode capacitance as described below) for a closed seal than for an opened seal.

The electronics described above communicate with other electronics provided within the PD apparatus. For example, the oscillator chip and associated electronics can be provided on a printed circuit breaker ("PCB"), which forms one of a plurality of controllers within the dialysis machine. The controller communicates with an, e.g., a supervisory, controller or central processing unit ("CPU"), which upon the detection of an un-opened bag receives a signal indicating that the bag is un-opened and that therapy at that point is unsafe. The supervisory controller or CPU can cause an alarm to sound and take any other appropriate action, such as occluding one or more line (e.g., patient or supply line) or halting a pump until the bag is opened.

The present disclosure also includes a capacitance sensing station for multiple dual or multi-chamber solution bags. The station stores or holds the bags during treatment. In any embodiment herein, the capacitor electrodes can be positioned to sense supply bags having three or more chambers. Further, in any embodiment herein, the capacitance systems can be positioned anywhere from horizontal to vertical for different bag arrangements and for air handling purposes.

The present disclosure includes other apparatuses and methods for distinguishing between the profile of a closed or sealed multi-chamber bag and that of an opened multi-chamber bag. For example, the capacitance sensors can be replaced with force or light-bean sensors that are positioned to detect the presence or absence of a closed seal. These additional sensors also rely on the different profiles a pinched (closed) or unpinched (opened) dual or multi-chamber bag.

It is therefore an advantage of the present disclosure to provide an improved medical fluid system.

It is another advantage of the present disclosure to provide an improved multi-chamber bag open seal check system and method.

It is a further advantage of the present disclosure to provide a multi-chamber bag open seal check system that uses the time that the multi-chamber bag is placed on a heater.

It is yet another advantage of the present disclosure to provide a multi-chamber bag open seal check system that uses capacitive sensing, force or light sensing.

It is still a further advantage of the present disclosure to provide a multi-chamber bag open seal check system that is automatic and does not relay on a visual check.

Additional features and advantages are described herein, and will be apparent from, the following Detailed Description and the figures.

BRIEF DESCRIPTION OF THE FIGURES

FIGS. 4A and 4B are sectioned elevation views of one embodiment of the heater of FIG. 3, showing a dual chamber bag closed and opened, respectively, creating different capacitive output profiles.

FIGS. 5A and 5B are oscilloscope outputs showing the difference in capacity (voltage) and frequency for the closed and opened dual chamber bag states of FIGS. 4A and 4B.

FIG. 5C is a schematic diagram illustrating how average voltage is determined using the outputs shown in FIGS. 5A and 5B.

FIG. 5D is a schematic diagram illustrating one suitable low pass filter ("LPF").

FIG. 5E is a diagram showing the calculated and measured average voltages for the outputs of FIGS. 5A and 5B using the analysis and apparatus of FIGS. 5C and 5D.

FIG. 6 is a perspective view of one embedment for an insulated electrode shown in FIG. 3 for capacitive sensing.

FIGS. 8A to 8D illustrated an alternative multi-bag system using capacitive sensing.

FIG. 9 is a plan view of an alternative heater or mat, which uses force sensors.

FIG. 10 is a plan view of an alternative heater or mat, which uses light sensors.

DETAILED DESCRIPTION

Figure 1:
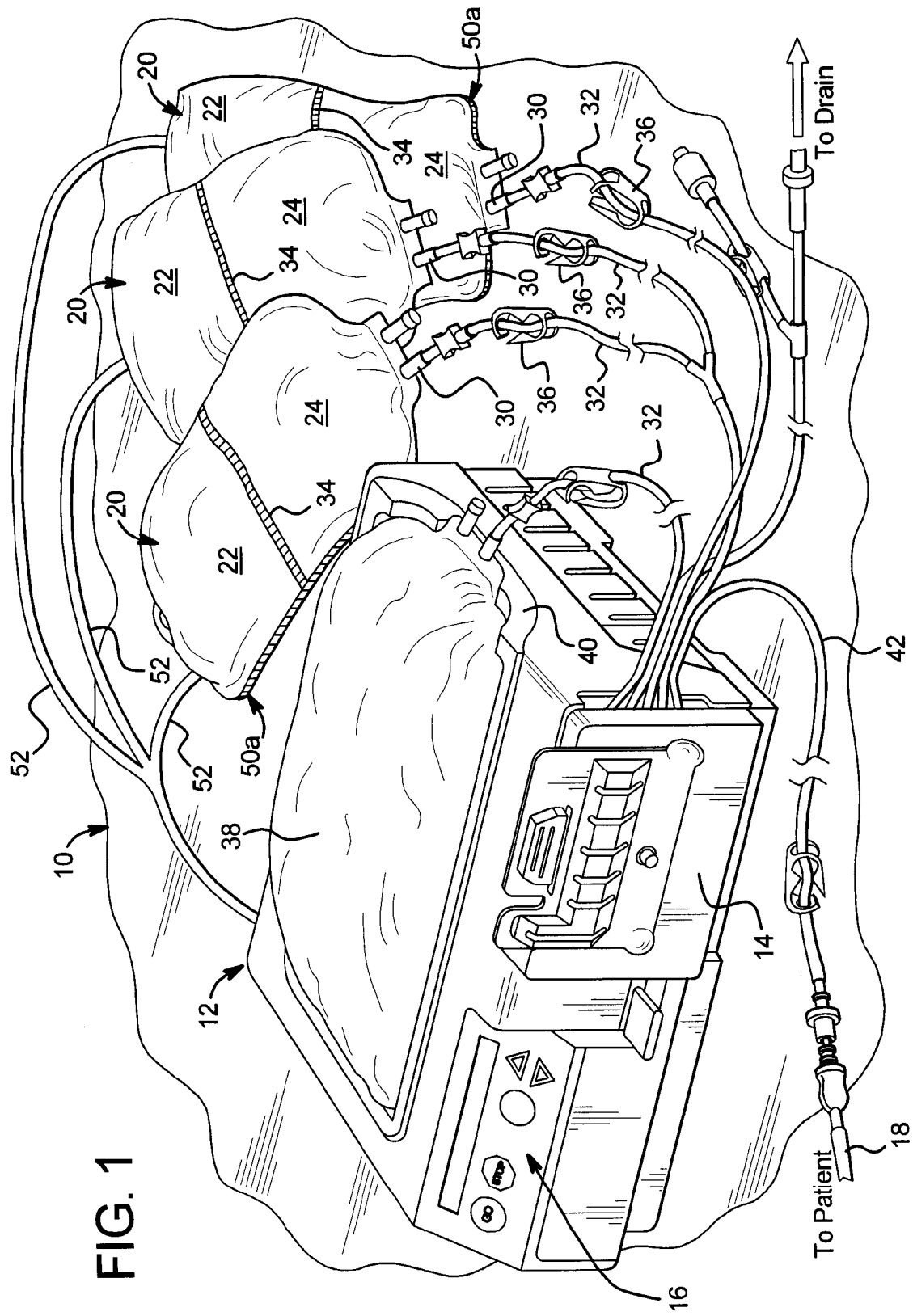
FIG. 1 is a perspective view of one embodiment of an automated peritoneal dialysis ("APD") system using dual chamber bags, and a heater bag and open seal check mats that employ a system and method for determining if a dual chamber bag has been opened properly.

Referring now to the drawings and in particular to FIG. 1, an automated peritoneal dialysis system 10 showing one embodiment for an open seal check system and method is illustrated. System 10 shows an automated peritoneal dialysis ("APD") system, which includes a cycler 12, which interacts with a liquid supply (bags 20) and a cassette (hidden behind panel 14 of system 10) to pump liquid from the supply and through the cassette. Cycler 12 also interacts with a control unit 16 that governs the interaction to perform a selected automated peritoneal dialysis ("APD") procedure. In the illustrated embodiment, cycler 12 and control unit 16 are located within or on a common housing. It should be appreciated however that the open seal check systems and methods illustrated herein are not limited to APD and apply to other types of peritoneal dialysis, such as continuous ambulatory peritoneal dialysis ("CAPD") and continuous flow peritoneal dialysis ("CFPD"). The open seal check systems and methods illustrated herein are also applicable to any blood treatment using bagged dialysate, such as hemodialysis ("HD"), hemofiltration ("HF"), hemodiafiltration ("HDF") and continuous renal replacement therapy ("CRRT").

Cycler 12 in one embodiment is durable and capable of long term and relatively maintenance free use. Cycler 12 also presents a compact footprint, suited for operation upon a table top or other relatively small surface normally found in the home. Cycler 12 is also relatively lightweight and portable.

The cassette is in one embodiment a single use, disposable item. The user loads the cassette into cycler 12 before beginning each APD therapy session. The user removes the cassette from cycler 12 upon the completing the therapy session and discards it.

In use (as shown in FIG. 1), the user connects the cassette to his/her indwelling peritoneal catheter 18. The user also connects the cassette to individual bags 20 containing sterile peritoneal dialysis solution for infusion. The cassette further connects to a bag 22 containing dialysis fluid, which a heater 40 heats to a desired temperature (typically to about 37° C.) before infusion into the patient.

Control unit 16 paces cycler 12 through a prescribed series of fill, dwell, and drain cycles typical of an APD procedure. During the fill phase, cycler 12 infuses heated dialysate through the cassette and into the patient's peritoneal cavity. Following the dwell phase, cycler 12 institutes a drain phase, during which cycler 12 discharges spent dialysis solution from the patient's peritoneal cavity through the cassette into a nearby drain (not shown).

As shown in FIG. 1, cycler 12 does not require hangers for suspending source solution bags 20 at a prescribed head height above it. This is because cycler 12 in the illustrated embodiment uses a pumping action, e.g., pneumatic, mechanical or a combination thereof, cycler 12 emulates gravity flow, even when the source solution bags 20 lie at a same or lower elevation as cycler 12. It should be appreciated however that cycler 12 is but one type of PD apparatus useable with system 10. Open seal check system 10 can be used alternatively with a gravity fed weigh scale or other system for pumping or volumetric control.

In the illustrated embodiment, cycler 12 establishes in essence an artificial head height, and has the flexibility to interact with and adapt quickly to the particular physiology and relative elevation of the patient. The relatively compact nature and quiet, reliable operating characteristics of cycler 12 make it well-suited for bedside use at home while the patient is asleep.

Solution bags 20 as seen in FIG. 1 are dual chamber bags but can alternatively have three or more chambers. Dual chamber bags 20 include first and second chambers 22 and 24, which hold first and second fluids 26 and 28 (FIGS. 4A and 4B). The cassette is connected to bags 20 via an access port 30 attached to the bags and supply lines 32 running from bags 20 to the cassette. As seen, access port 30 for each bag 20 is connected fluidly to chamber 24. When it is desired to use the combined solution within bags 20, a frangible seal 34 having a pinched seam is broken allowing the solution from chamber 22 to mix with the solution from chamber 24. The mixing is done before supply lines 32 are connected to bags 20 and/or before clamps 36 on supply lines 32 are opened.

In FIG. 1, cycler 12 pumps mixed fluid from supply bags 20, through ports 30, supply lines 32 and the cassette to a warmer bag 38. Warmer bag 38 is placed on a heater 40 powered by cycler 12. Mixed fluid resides inside warmer bag 38 until it is heated to a desired, e.g., body temperature. Afterwards, cycler 12 pumps heated fluid through the cassette, out a patient line 42 to indwelling catheter 18.

In FIG. 1, an open seal check system 50a in the form of an access disconnection mat is placed beneath each dual chamber bag 20. Open seal check system 50a outputs to control unit 16 via cables 52 in the illustrated embodiment. Alternatively, open seal check systems 50 outputs to control unit 16 wirelessly, e.g., through radio frequency ("RF"), encoded RF or secure Bluetooth technology.

The operation of open seal check system 50a is described in more detail herein. The output in one embodiment is a voltage and frequency, which is dependant upon at least on capacitance measured at each bag 20. Control unit 16 includes at least one processor that receives the signal outputs from open check system 50a. The processor operates with software located within control unit 16 to determine whether the voltage and frequency correspond to a bag-open condition or a bag-closed condition. If the processor determines that dual chamber bag 20 is open, therapy can continue. If the processor determines that dual chamber bag 20 is not open, the processor takes one or more preventive actions, such as: (i) sounding an alarm, (ii) causing cycler 12 to occlude supply lines 32 and/or patient line 42 and (iii) preventing a pump actuator of cycler 12 from operating with the cassette to pump fluid.

Figure 2:
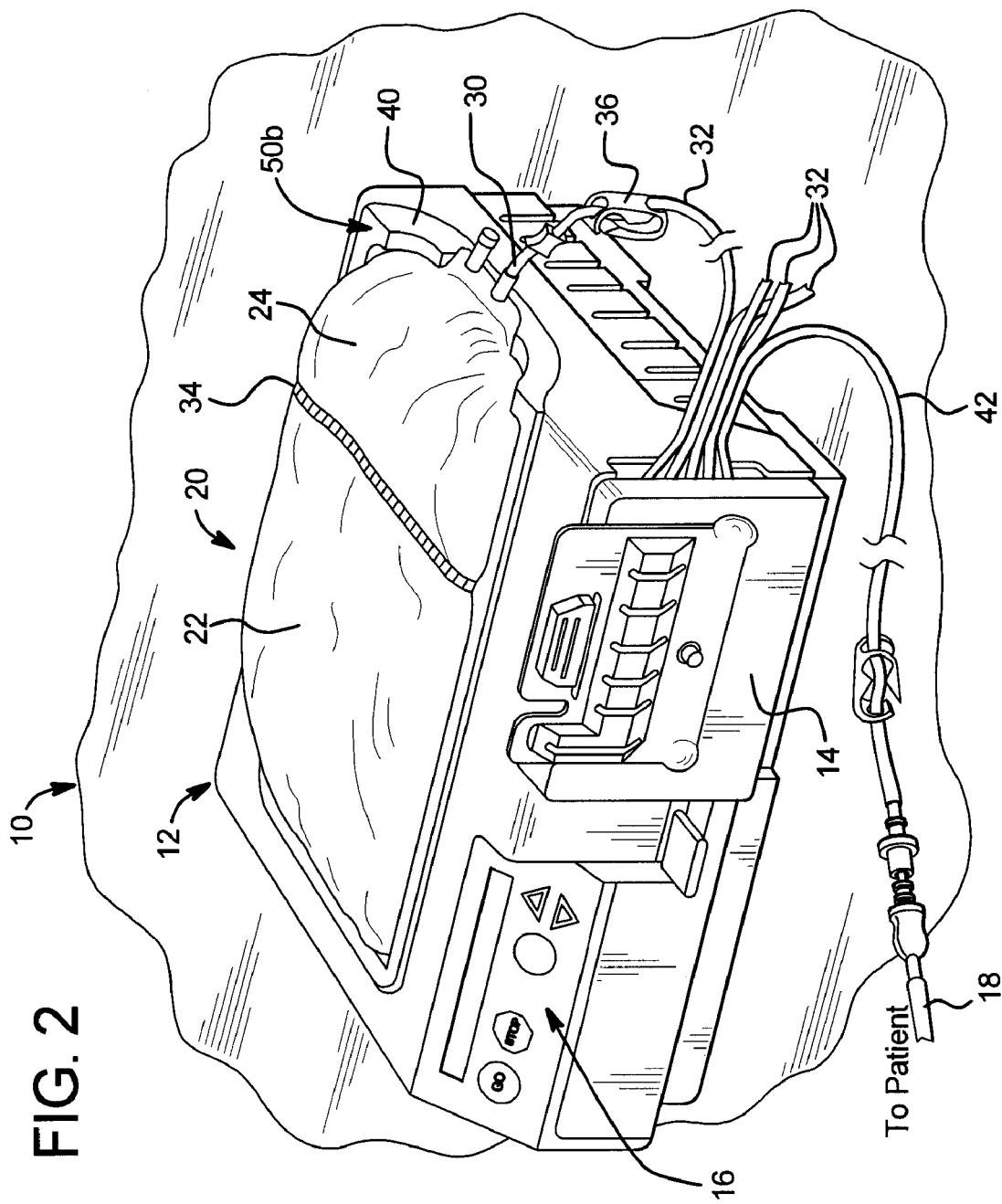
FIG. 2 is a perspective view of one embodiment of an automated peritoneal dialysis ("APD") system that uses a heated dual chamber bag and heater that employs a system and method for determining if a dual chamber bag has been opened properly.

Open seal check system 50b of FIG. 2 is similar to system 50a FIG. 1. Here however warmer bag 38 is not used and supply bags 20 are loaded directly onto heater 40. Open check system 50b is accordingly incorporated into heater 40. Heater 40 in the illustrated embodiment is a resistive batch type heater. Heater 40 can alternatively use different heating technologies, such as convective heating or radiant heating. The output of open seal check system 50b in one embodiment is wired internally to control unit 16. If heater 40 is located in a unit separate from cycler 12, and dual or multi-chamber bag 20 is loaded directly on the separated heater, system 50b can communicate with control unit 16 via any of the hard-wired or wireless methods described above for system 50a.

The operation of open check system 50b is described in more detail herein. The output in one embodiment is again a voltage and frequency, which is dependant upon capacitance measured at bag 20. If the processor within control unit 16 after receiving the voltage and frequency output from system 50b determines that dual chamber bag 20 is open, therapy can continue. If the processor determines that dual chamber bag 20 is not open, the processor takes one or more of the preventive actions discussed above.

Figure 3:
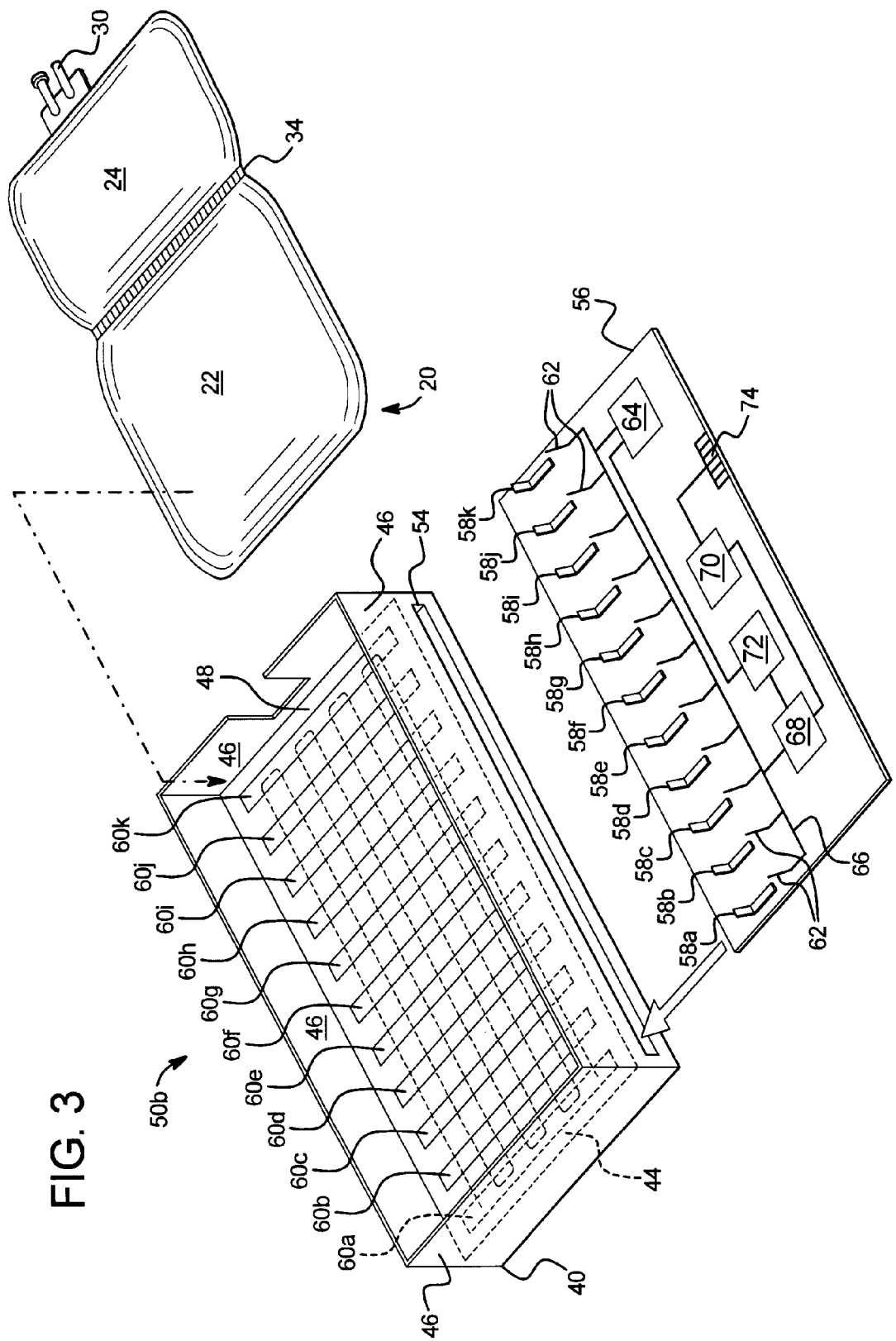
FIG. 3 is a perspective view of one embodiment of the heater of FIG. 2, which uses insulated conductive strips or electrodes for capacitive sensing.

Referring now to FIG. 3, system 50b illustrates one embodiment of an open seal check system using capacitive sensing. As discussed above, system 50b operates with a heater 40. Heater 40 in the illustrated embodiment includes heating coils 44, which are shown as dashed or hidden in FIG. 3. The teachings associated with system 50b in FIGS. 3, 4A, 4B, 5A, 5B, 6 and 7 are also applicable to the open seal check mat 50A of FIG. 1. The primary difference with the two systems is in their implementation. Open check mat 50a does not have heating coils 44 or other heating apparatus and does not heat fluid within dual chamber bags 20.

Dual chamber bag 20 is shown for reference in FIG. 3. Heater 40 includes raised side walls 46 that position dual chamber bag 20, such that frangible or peel seal 34 of dual chamber bag 20 is aligned with one of the capacitance strip or electrodes 60a to 60k fitted with a pan 48 of heater 40. Pan 48 supports dual chamber bag 20 and conducts heat into fluids 26 and 28 (FIGS. 4A and 4B) of chambers 22 and 24, respectively. A front wall 46 defines a notch, which provides room for access to access port 30 of dual chamber bag 20.

Open check system 50b is shown having a slot 54 for receiving a controller 56. Controller 56 is placed such that contacts 58a to 58k make electrical contact with a portion of the capacitances electrodes or plates 60a to 60k, respectively. Contacts 58a to 58k are further positioned to make electrical contact with switches 62. A multiplexer 64 is provided which closes switches 62 sequentially, such that readings from capacitance plates 60a to 60k are taken at desired times. Signals from capacitance plates 60a to 60k travel through a respective contact 58a to 58k and switch 62 to a common trace 66.

Controller 56 can but does not have to include signal conditioning 70, such as a low pass filter and an analog to digital ("A/D") converter, which conditions a signal that is outputted to an astable multi-vibrator 68 in one embodiment. Astable multi-vibrator 68 in an embodiment is an NE556 astable multi-vibrator, which provides two oscillators, one used as a free-run oscillator and another used as a mono-stable oscillator. Another suitable astable pulse generator is provided by Hitachi, HA17555 series. This pulse generator has a single oscillator. Therefore, two Hitachi, HA17555 series vibrators could be used, one as the free-run oscillator and another as the mono-stable oscillator. Astable multi-vibrator 68 and associated capacitors formed via electrodes 60 (referring collectively to electrodes 60a to 60f for example) form an oscillating circuit, shown in more detail below in connection with FIG. 7. Using astable multi-vibrator 68, the oscillating circuit is caused to oscillate at its intrinsic frequency, which depends on the capacitance of the measuring capacitor formed via conductive liquid 26/28 the dielectric therebetween and one of electrodes 60. The capacitance depends on the combination of dielectric materials as discussed above.

A stable multi-vibrator 68 outputs an oscillating voltage at a frequency for each electrode or capacitance plate 60a to 60k. The voltage and frequency are indicative of a capacitance between each electrode (acting as a first capacitor plate) and the relatively conductive medical fluid (acting as a second capacitor plate), wherein the material of multi-chamber bag 20, the insulation surrounding the conductive of electrodes 60 and potentially air between the heater (or mat) and the bag (at the peel seal) forms a dielectric between the capacitor plates. Astable multi-vibrator 68 outputs the signal to a controller or central processing unit ("CPU") located within cycler 12. Cycler 12 includes processing that interprets the signal and reacts accordingly. In an alternative embodiment, controller 56 has a processor (not illustrated) that processes the signal for the CPU.

Controller 56 further includes a power supply 72, such as a DC power supply, that supplies power to any one or more of multiplexer 64, signal conditioning 70 and astable vibrator 68. Contact area 74 is configured to be connected electrically with additional electrical equipment located within cycler 12, such as the CPU. In one embodiment, controller 56 is a sub-controller that outputs to a CPU within cycler 12. The CPU can be one of multiple CPU's that cycler 12 uses. Signal conditioning 70 (such as a low pass filter and A/D converter) can also be performed on a remote controller. Controller 56 in one embodiment is printed circuit board ("PCB") based, such that contacts 58a to 58k, switches 62, trace 66, multiplexer 64, signal conditioning (if any), astable vibrator 68, power supply 72 and contact area 74 are either soldered to the PCB or etched onto the PCB.

While controller 56 is shown as being inserted into heater 40, in an alternative embodiment controller 56 is located within cycler 12, and separate from the heating module, but wherein contacts 58a to 58k are positioned to make electrical contact with the electrodes or capacitance plates 60a to 60k of heater 40. Further, while controller 56 is shown with contacts 74 for hard-wiring to control unit 16, controller 56 can alternatively communicate with another control apparatus wirelessly. For example, the external mat 50a can have an embedded controller 56 and an, e.g., radio frequency ("RF") transceiver that communicates two-way and wirelessly with control unit 16 of cycler 12.

Referring now to FIGS. 4A and 4B, the operation of capacitance open-check system 50 (referring collectively to systems 50a and 50b) is illustrated. System 50 is illustrated using heater 40 described in connection with FIG. 3. Those of skill in the art should appreciate however that the heater apparatus is not necessary to perform the capacitance sensing described herein and that system 50 can be configured alternatively as a mat, or other supporting apparatus, which is placed beneath dual chamber bags 20 as shown in FIG. 1. In FIGS. 4A and 4B, open check system 50 includes six contacts 58a to 58f, which each contact one of six electrodes 60a to 60f, respectively. FIG. 3 shows eleven electrodes and contacts.

It should be appreciated that the number of electrodes can be varied as needed to provide enough capacitance data to detect whether dual chamber bag 20 has been opened or not. Furthermore, the sensing systems described herein are not limited to detecting only dual chamber bags. There are currently bags with three and four chambers on the market. It is accordingly expressly contemplated to provide as many electrodes 60 as needed and at positions on pan 48 appropriate for detecting whether the second and possibly third seals of the multiple chamber bag have been opened or not.

FIG. 4A shows dual chamber bag 20 with a peel seal or frangible seal 34 intact. FIG. 4B shows dual chamber bag 20 after frangible seal 34 has been opened. Accordingly, dual chambers 22 and 24 of FIG. 4A are shown as a single chamber 22/24 in FIG. 4B. Further, separate fluids 26 and 28 in FIG. 4A are shown as a single mixed fluid 26/28 in FIG. 4B.

The capacitance open seal check system 50, and indeed each of the open check systems described herein, takes advantage of the difference in profile shapes between the closed and opened bag 20, as seen by the cross sectional elevation views of FIGS. 4A and 4B. As seen in FIG. 4A, peel seal or frangible seal 34 resides a distance "d" vertically above panel 48 (electrode 60d in the illustrated example). The bag at other electrodes generally lies on heater plate or panel 48, such as at electrodes 58a, 58b, a portion of electrode 58c and electrode 58f. In FIG. 4B however opened back 20 lies flat across all of electrodes 58a to 58e placed on top of or embedded within heater plate or panel 48. There may however be a small gap "d" remaining at the opened peel seal area.

Electrodes 60a to 60e in an embodiment are insulated, e.g. coated with a high melting-temperature plastic, such as high temperature teflon. Multiplexer 64 in the illustrated embodiment causes astable multi-vibrator 68 to sequence through and sense a capacitance $C_{60a}$ to $C_{60f}$ corresponding to each electrode 60a to 60f. Liquids 26 and 28 or combined liquid 26/28 is relatively conductive and forms in essence a first capacitor plate. The plastic of dual chamber bag 20, the plastic coating around electrodes 60a to 60f and the air gap "d" that peel seal or pinched seam 34 forms above panel 48 forms a dielectric. Conductive electrodes 60a to 60f form a second capacitor plate. When dual chamber bag 20 is opened, air gap "d" goes away or diminishes substantially, changing the dielectric and resulting capacitance output.

As seen in FIG. 4A, the capacitance $C_{60d}$ measured at electrode 60d separated by at gap distance "d" is considerably less than the capacitance $C_{60f}$ measured at electrode 60f (could use capacitances sensed from any of electrodes 60a, 60b in FIG. 4A alternatively). Also, the frequency of the signal measured at electrode 60d will be higher than the frequency of the signal measured at, e.g., electrodes 60a, 60b or 60f. Thus, either an output voltage indicative of capacitance or a frequency of the measured signal can be used to differentiate between an area in which dual-chamber bag 20 forms a gap distance "d" and an area of bag 20 lying on panel 48.

In FIG. 4B, after bag 20 has been opened, gap distance "d" above electrode $C_{60d}$ disappears or is diminished greatly. Accordingly, the capacitance 60d measured at electrode 60d is, in the case of FIG. 4B, only slightly less than or approximately equal to the capacitance C at electrodes 60a, 60b or 60f. The capacitance open seal check system 50 in one embodiment looks to the capacitance 60d at electrode 60d (or the peel seal capacitance), knowing that peel seal 34 is always positioned above electrode 60d (due to bag size consistency, walls 46 and set orientation due to access port 30) to determine whether peel seal 34 has been opened or not. Alternatively, using multiple electrodes, capacitance open seal check system 50 sequences through multiple electrodes and looks for a change or delta in capacitance measured from different electrodes 60 to determine whether peel seal 34 has been opened or not. It is therefore contemplated in one embodiment to provide enough electrodes 60 centered about the normal positioning of peel seal 34 to ensure that peel seal 34 will reside above one of the capacitors 50. As illustrated in FIG. 3, electrodes 60 are positioned so as to be at least substantially parallel with peel seal 34.

FIGS. 4A and 4B show bag 20 lying at least substantially horizontally on pan 48. It should be appreciated however that pan 48 and thus heater 40 can be set at an angle, e.g., with the side having access port 30 being elevationally lower than the opposite side. The angled bag orientation uses gravity to help first fluid 26 to flow from compartment 22 to mix with second fluid 28 in compartment 24. The angled orientation also tends to allow air to migrate towards the upper edge of compartment 22, while only fluid leaves the lower positioned port 30, which is desirable.

It is also possible that multi-chamber bag is oriented vertically or almost vertically such that the bag is pressed or rests against a vertical sensing wall. A sensor is placed at pinched or peel seal 34. When seal 34 is opened, the bag moves closer or against the vertical wall causing a change in capacitance, which is sensed.

Figure 5B:
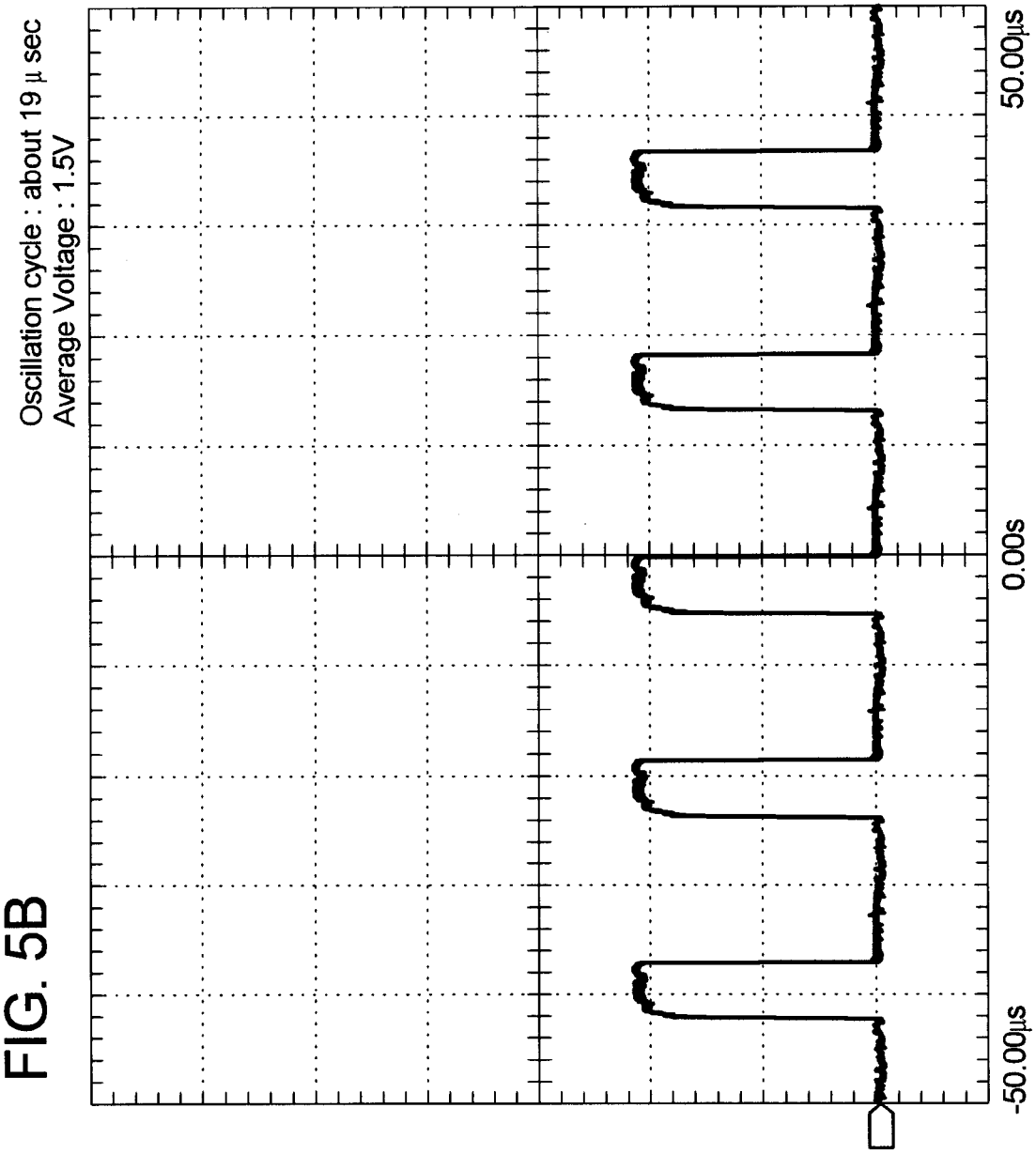

Referring now to FIGS. 5A and 5B, actual outputs from a test preformed using the oscillating circuit of FIG. 7 are shown for the states in which dual chamber bag 20 is closed (FIG. 5A) and opened (FIG. 5B), which, correspond to the states in FIGS. 4A and 4B, respectively. In the graph of FIG. 5A (when peel seal 34 is closed), the oscillation frequency is about sixteen microseconds and the average voltage (indicative of the capacitance at the electrode placed beneath peel seal 34) is about 1.85 volts. In FIG. 5B, (when peel seal has been opened), the same electrode generates a signal having a frequency of about nineteen microseconds and a voltage (indicative of capacitance at the electrode) of about 1.5 volts. This difference in voltage and/or frequency can be used to detect whether peel seal 34 has been opened or not.

The average voltage output as seen on the graphs of FIGS. 5A and 5B is inversely proportional to the corresponding capacitance for the electrode detected. Thus the decreasing average voltage in FIG. 5B is due to an increasing capacitance at the electrode when the bag is opened, which is consistent with the analysis of $C_{60d}$ and $C_{60f}$ shown in connection with FIGS. 4A and 4B. That is, as the capacitance at electrode 60d increases due to the reduced dielectric caused by the diminishment of gap "d," astable multi-vibrator 68 responds by outputting a decreasing average voltage to, for example, control unit 16 of instrument 12. Also, the frequency of the signal decreases when the bag is opened from one cycle every sixteen seconds to one cycle every nineteen seconds. Thus, average voltage and/or frequency, both related to capacitance, can be used to detect whether the frangible seal has been opened.

FIG. 5C illustrates how average voltage is determined in FIGS. 5A and 5B. The average voltage is determined as follows:

$V_{average} = T_c/T * V_p$, where $T_c$=the pulse high level period (length of upper horizontal lines of graphs of FIGS. 5A and 5B, e.g., in microseconds), T=period of one total cycle (e.g., microseconds), and Vp=pulse peak voltage.

FIG. 5C shows that to measure $V_{average}$, a low pass filter ("LPF") is used. For the case with a closed seal, a relatively small capacitance and relatively high free-run frequency ($T_c$ is 0.8 T) yields a relatively high LPF output (e.g., for $V_p$=5V, $V_{average}$=4V). For the case with an open seal, a relatively large capacitance and relatively low free-run frequency ($T_c$ is 0.4 T) yields a relatively low LPF output (e.g., for $V_p$=5V, $V_{average}$=2V). This difference in measured average voltage is detachable and repeatable, providing a suitable open seal check system.

Figure 7A:
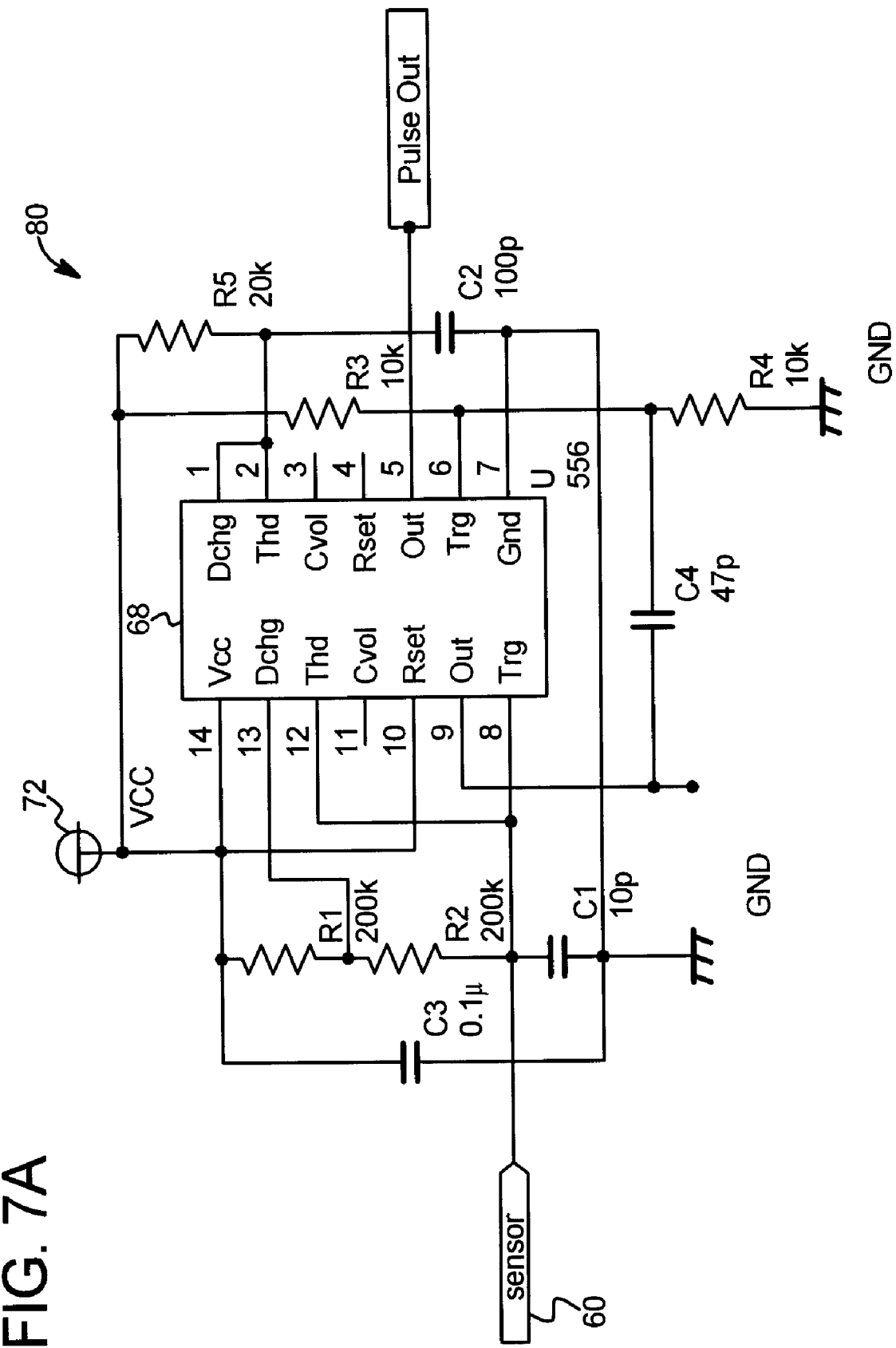
FIG. 7A is one embodiment of an electrical layout for the capacitive system of FIGS. 3, 4A, 4B, 5A, 5B and 6.

FIG. 5D illustrates an example of a LPF, which includes a resister between the input of the filter and "pulse out" shown in FIG. 7A. As seen in FIG. 5D, LPF further includes a capacitor between the resister path and ground.

FIG. 5E shows a table using the analysis and apparatus set forth in FIGS. 5C and 5D to analyze the output of FIGS. 5A and 5B. For FIG. 5A, with a closed seal, a relatively small capacitance, $T_c$=6.4 microseconds, T=16 microseconds, $V_p$=4.5V, a calculated $V_{average}$=1.8V and a measured $V_{average}$=1.85 V. For FIG. 5B, with an opened seal, a relatively large capacitance, $T_c$=6.4 microseconds, T=19 microseconds, $V_p$=4.5V, a calculated $V_{average}$=1.52V and a measured $V_{average}$=1.5 V. Thus the measured $V_{average}$ using the circuitry described herein tracks the predicted $V_{average}$ closely. Further, the circuitry and associated system is shown to be able to detect between a closed bag and an opened bag.

Referring now to FIG. 6, an embodiment for electrode 60 is illustrated. Electrode 60 referrers generally to any of the electrodes 60a to 60k disclosed herein. Electrode 60 includes a conductor 76, such as a copper or other suitable metal strip. Conductor 76 in an embodiment runs the length of electrode 60. Electrode 76 can be made of any suitable conductive material. Electrode 76 is coated with an insulative coating 78, such as a high temperature nylon coating, which can withstand the temperatures of heater 40. In an embodiment in which electrode 60 is provided with a bag supporting mat as shown in connection with FIG. 1, insulative coating 78 is not required to be high temperature. An aperture or opening 82 is formed in insulation 78 to allow conductor 76 to make an electrical connection with a contact 58 (referring to any of the contacts 58a to 58k) shown above in connection with controller 56 of FIG. 3. The width and thickness of electrodes 60 are configured so as to impede the heating ability of heater 40 as little as possible. Further, the number of electrodes 60 can be minimized about peel seal 34 to ensure that heating effectiveness is maximized.

Figure 7B:
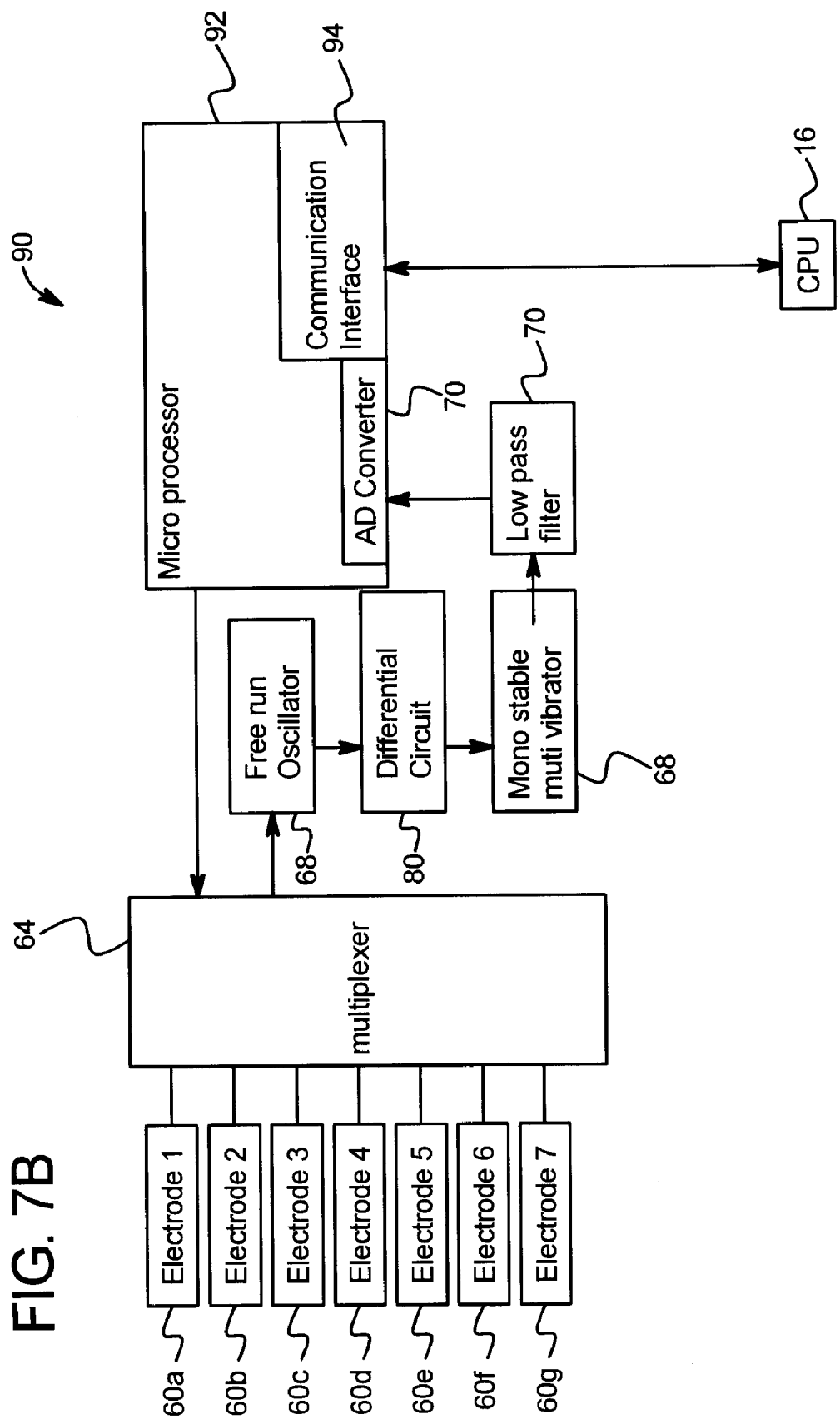
FIG. 7B is one embodiment of a control scheme for the capacitive system of FIGS. 3, 4A, 4B, 5A, 5B and 6.
Figure 7C:
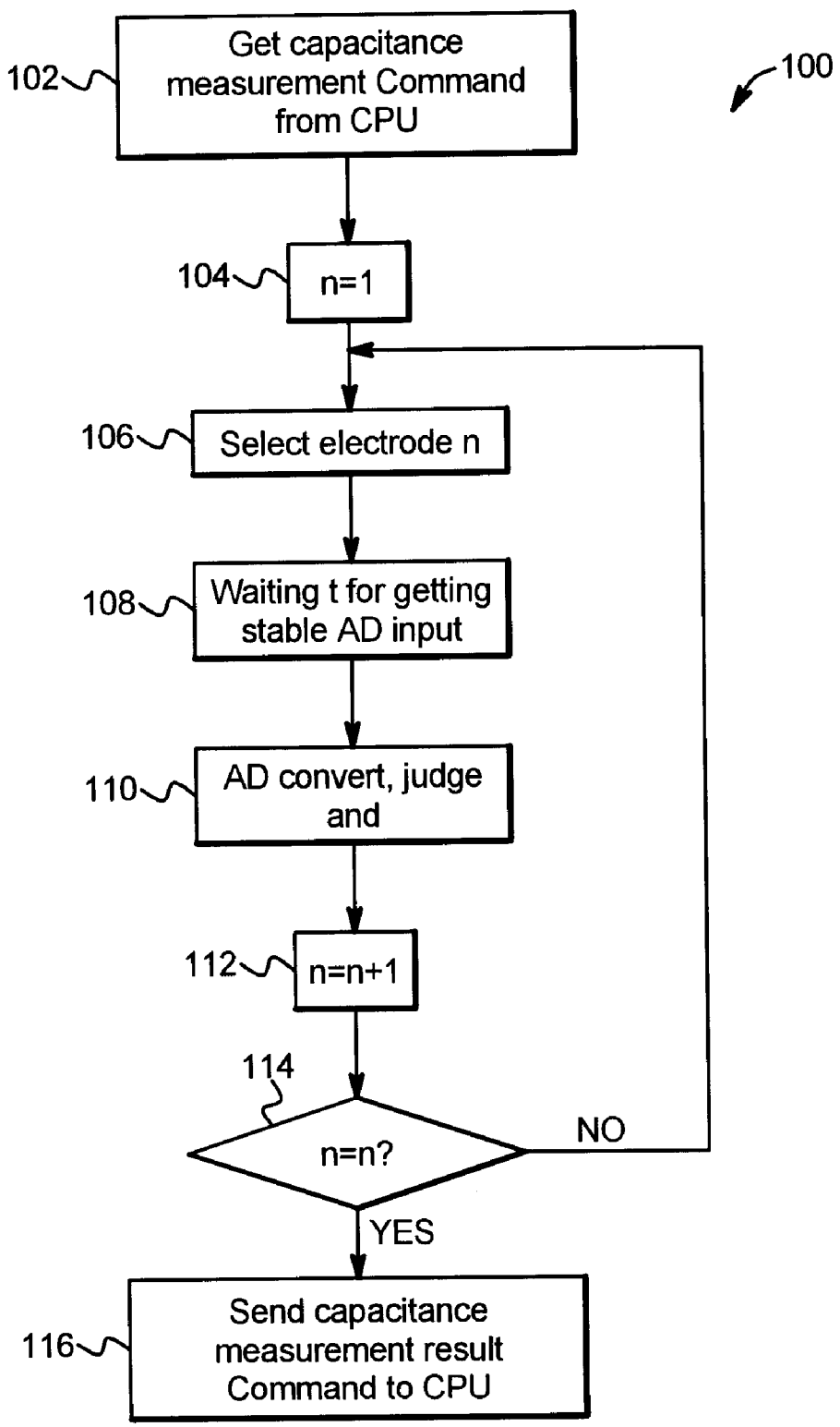
FIG. 7C is one embodiment of a logic flow diagram for the capacitive system of FIGS. 3, 4A, 4B, 5A, 5B and 6.

Referring now to FIGS. 7A to 7C, the electronics, control scheme and logic flow for the capacitance sensing embodiment are illustrated, respectively. FIG. 7A shows a an electrical diagram 80, which has a sample oscillating circuit. Circuit 80 shows a sensor 60, voltage supply $V_{cc}$ from power source 72, astable multi-vibrator 68 and a pulse output to for example control unit 16 of instrument 12. Multi-vibrator 68 as discussed above includes two oscillators. The two oscillators can be provided in a single, dual-oscillator package (e.g., NE556) or via two single oscillator pulse generators (e.g., two HA17555 devices). In either case, one of the oscillators is used as a free-run oscillator. The other oscillator is used as a mono-stable multi-vibrator. The operation of each of these is discussed below.

In FIG. 7A, resistors R1 and R2 and capacitor C1 in combination with the electrode capacitance decide or control the frequency of the free-run oscillator of multi-vibrator 68. Capacitor C4 and resistors R3 and R4 form a differential circuit, which is described in more detail below. The output of the differential circuit is fed to pin 6 of the mono-stable multi-vibrator 68. The time constant of the mono-stable multi-vibrator is set by capacitor C3 and resistor R5.

Referring now to FIG. 7B, a block diagram illustrates one embodiment for a control scheme of the capacitive sensing open-seal check system. In control scheme 90 of FIG. 7B, multiplexer 64 samples through electrodes 60a to 60g. From multiplexer 64, the free-run oscillator of multi-vibrator 68 generates a first rectangular wave, which has a frequency that depends on an equivalent capacitance. Equivalent capacitance is a sum of a stray (environmental) capacitance and an electrode capacitance. Higher electrode capacitance corresponds to the liquid being closer to the electrodes 60, e.g., the condition of FIG. 4B. Higher equivalent capacitance corresponds to a lower frequency signal. Thus lower average voltage (higher electrode capacitance) of the signal and lower frequency are indicative of a bag-open state, while the reverse is true for a bag-closed state.

As seen in FIG. 7B, the first rectangular wave of the free-run oscillator of multi-vibrator 68 passes through the differential circuit (C4, R1 and R2 of electrical diagram 80 of FIG. 7A). The output of differential circuit (C4, R1 and R2) is fed to the trigger gate of the mono-stable oscillator or vibrator 68 (e.g., at pin 6). The timing of the differential circuit is equal to the falling edge of the square wave from the free-run oscillator of astable multi-vibrator 68.

The mono-stable multi-vibrator of astable multi-vibrator 68 generates a second rectangular wave, which has a time constant width ($T_c$) high level and a variable width low lever, wherein the variable width low level depends on the equivalent capacitances described above. Low pass filter 70 in FIG. 7B generates a DC level equal to the average voltage set by the equivalent capacitance as seen in FIGS. 5A and 5B. Multiplexer 64 gives each electrode enough time e.g., about 0.1 second, to ensure that a stable DC level is sensed.

The output of low pass filter is sent to A/D converter 70, which can be a stand-alone component (e.g., as in FIG. 3) or provided with a microprocessor 92 as seen in FIG. 7B. Microprocessor 92 also includes a communication interface 94, which can be hard-wired or wireless transceiver, as described above. Communication interface 94 provides two-way communication with the CPU, e.g., of control unit 16 (FIGS. 1 and 2).

Referring now to FIG. 7C, a logic flow diagram 100 for the capacitance sensing open-seal check system is illustrated. Sequence 100 is performed for example by a microprocessor, such as microprocessor 92 of FIG. 7B, which can be located with the heater controls of system 10, located with its safety controller, be located externally, e.g., with mat system 50a, and/or with control unit 60 of cycler 12.

In step 102, CPU of control unit 60 sends a command to the microprocessor to begin taking capacitance readings. This can occur before therapy has begun and/or during therapy. The test can be triggered automatically, for example, upon sensing that a pumping cassette connected to tubing 32, 42 and operable with cycler 12 has become pressurized with fluid.

A count n is set to one as seen at step 104. The count corresponds to one of the electrodes 60, that is, each electrode has a different count or number. Sequence 100 selects an electrode with count n (step 106) and waits for a sufficient time t to ensure that, e.g., digitized, DC input from the sensor is stable as seen at step 108.

Once a stable signal is obtained, sequence 100 determines whether the particular electrode 60 is in a bag-open state or a bag-closed state (per signal characteristics discussed above), as seen at step 110. Sequence 100 increments count n (step 112) and repeats steps 106 to 112 until the count reaches the total number of electrodes (step 114).

Sequence 100 sends a capacitance measurement output (e.g., average voltage and frequency) to control unit 16, e.g., the CPU (or alternatively the safety controller), of control unit 16. In an embodiment, if any of electrodes 60 senses a bag-closed state (e.g., capacitance below set point (voltage above set point) and/or frequency above set point), system 10 sends an audio, visual or audio-visual message to the patient or operator. System 10 can also lock (pump and/or valves) cycler 12 such at it will not pump fluid until each of sensors 60 reads bag-open. To this end, control unit 16 can provide a manual input, which the patient or caregiver can press after opening bag 20 properly and receiving clearance from open-check system 50 to allow therapy to continue.

Referring now to FIGS. 8A to 8D, an alternative multi-bag system 120 using capacitance sensing is illustrated. As discussed above, the capacitance peel seal check systems herein can be expanded to check three and four chamber bags if desired. Here, another alternative system operates with multiple bags, which each can be dual chamber bags 20 or three or four chamber bags as discussed above. For convenience, FIG. 8A shows a dual chamber bag 20.

System 120 can be used in cooperation with a bag heater, similar to system 50. Alternatively, system 120 doubles as a bag management system, which holds multiple bags needed for an entire therapy. The bags can feed to a separate warmer bag or inline heater to heat the fluid to a desired treatment temperature. System 120 can tilt the bags away from horizontal as described above, e.g., with ports 30 being lower elevationally than the edges of compartment 22 for air handling purposes.

System 120 includes a plurality of cells 122a to 122e (referred to herein collectively as cells 122 or generally, individually as cell 122). Cells 122a to 122e are each separated by a sidewall 124. Sidewalls 124 are spaced apart a distance appropriate to fit a bag 20 within each cell 122. Sidewalls 124 each terminate at one end to an end wall 126 having cutouts 128 sized to hold ports 30 or tubes running from ports 30. Multi-bag system 120 can be made of any suitable material such as plastic or metal.

FIG. 8B illustrates that each cell 122 has its own one or more electrode or capacitance plate 130, which can be a conductive film with an insulating coating similar to that of the embodiment of FIG. 6. Each cell 122 is shown having a single electrode or capacitance plate 130 positioned for example to be inline with frangible seal 34 when bag 20 is loaded into the cell. Alternatively, one or more of the cells can have multiple electrodes or capacitance plates 130 as desired for a dual chamber bag 20 or a bag having three or more chambers. In FIG. 8B, cells 122 are shown as being generally u-shaped. The cells can alternatively be rectangular in cross section. Electrodes or capacitance plates 130 are placed on ridges 132 extending inwardly from the wall or walls for cells 122 in the illustrated embodiment but are alternatively placed on the that surfaces of cells 122.

FIG. 8C shows a top view of cells 112a to 112c, with cell 122b holding a dual chamber bag 20 having a closed peel seal 34. Peel seal 34 is aligned with electrode 130 of cell 122b. FIG. 8D shows cell 122b holding a dual chamber bag 20 with peel seal 34 opened. The capacitance sensed using electrode 130 will change as shown above, indicating that bag 20 has been opened.

FIGS. 8C and 8D also illustrate that system 120 serves a second purpose, namely, being able to tell which cells 122 have bags loaded and which ones do not. That is, the capacitance sensed via electrode 130 for a cell will change when a bag 20 is loaded into that cell versus a no-load condition regardless of whether the bag is opened or closed. System 120 can therefore determine for example if the patient has loaded enough solution for a given treatment.

Referring now to FIG. 9, system 150 illustrates an alternative open seal check system. System 150 is shown in connection with heater 40 having heating panel 48 and side walls 46. It should be appreciated however that system 150 is alternatively provided as a mat or other type of support surface for supporting a dual or multi-chamber bag 20 shown in FIG. 1. System 150 differs from system 50 primarily in that force sensors or strain gauges 152a to 152h in system 150 replace the capacitive sensing of system 50. Force sensors 152 (referring collectively to sensors 152a to 152h) are placed on or imbedded into panel 48 of heater 40 in a manner similar to the attachment of electrodes 60 of capacitance sensing system 50. Force sensors 152 lying under liquid within chambers 22 and 24 read a greater weight than a sensor 152 underlying closed peel seal 34, which will likely read no weight when an air gap resides directly above sensor 152d shown in FIG. 9. System 150 relies on the weight of the fluid and the situation in which bag 20 opens enough to contact sensor 152d when peel seal 34 is opened. When this happens, sensor 152d generates a positive weight read out, which is different than when peel seal 34 is intact. System 150 can also be used for bag versus no bag detection. The system can also be used in an angled or vertical application and with bags have three or more chambers.

FIG. 10 illustrates a further alternative open check system 250. System 250 is also shown in connection with heater 40 but can be used in a mat type application shown in FIG. 1. System 250 uses light emitters 252a to 252c, which each operate with a light receiver 254a to 254c. The emitters 252 (referring collectively to emitters 252a to 252c) are placed on an opposite side of heater 40 from receivers 254 (referring collectively to receivers 254a to 254c). Emitters 252 and receivers 254 are placed low enough elevationally within walls 46 such that fluid 26 and 28 within chambers 22 and 24 will block or change the amount of light received by receivers 254, but wherein gap "d" underneath peel seal 34 when the seal is closed will allow light to pass through substantially freely. When peel seal 34 is opened, fluid 26/28 within single chamber 22/24 changes the amount of light received by, e.g., receiver 254b in FIG. 10, enough to signal that peel seal 34 has been opened. System 250 can also be used for bag versus no bag detection. The system can also be used in an angled or vertical application and with bags have three or more chambers.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An open seal check system for a multi-chamber supply container having at least one elongated seal, the system comprising:
   a base contacting the multi-chamber container;
   at least one electrode positioned on the base so as to be aligned with the elongated seal; and
   electronics in operable communication with the at least one electrode, the at least one electrode forming at least one capacitor with the multi-chamber supply container when the container is placed on the base, the electronics configured to output a signal indicative of a dielectric associated with the at least one capacitor.

2. The open check seal system of claim 1, wherein the base is at least one of: (i) part of a medical fluid heater or a supportive apparatus; (ii) angled; (iii) vertically disposed; and (iv) configured to contact and sense a plurality of multi-chamber supply containers.

3. The open seal check system of claim 1, wherein the at least one electrode is at least one of: (i) insulated and (ii) a plurality of electrodes positioned at least substantially parallel to each other.

4. The open seal check system of claim 1, wherein the base is configured to perform at least one of: (i) orient the supply container such that the elongated seal is aligned with the at least on electrode, (ii) align the supply container such that the elongated seal is positioned at least substantially adjacent to the at least one electrode; (iii) align the supply container such that a plurality of electrodes can sense whether a plurality of seals have been opened.

5. The open seal check system of claim 1, wherein the electronics includes an oscillator, and wherein the signal includes at least one of a voltage and a frequency.

6. The open seal check system of claim 5, wherein the electronics includes at least one of: (i) a sequencer configured to sequence the oscillator through a plurality of the electrodes and output a signal for each corresponding capacitor; (ii) a free-run oscillator and a mono-stable multi-vibrator; (iii) a differential circuit; (iv) a low pass filter; (v) a time constant; and (vi) a voltage source.

7. The open seal check system of claim 1, wherein the dielectric is a function of at least one of: (i) a material of the multi-chamber supply container; (ii) insulation provided with the at least one electrode; and (iii) air.

8. The open seal check system of claim 1, wherein the electronics upon determining that the seal is unopened are configured to cause at least one of: (i) an alarm to be sounded; (ii) a line to be occluded; and (iii) a pump to be precluded from operation.

9. The open seal check system of claim 1, wherein the electronics are configured to compare different signals from the same at least one capacitor.

10. The open seal check system of claim 1, the signal being a voltage signal, the electronics configured to compare the voltage signal recorded at different times.

11. The open seal check system of claim 1, the signal having a frequency, the electronics configured to compare the frequency of the signal recorded at different times.

12. An open seal check system for a multi-chamber supply container having at least one elongated seal creating a pinched seam along the seal, the system comprising:
   a base contacting the multi-chamber container;
   at least one sensor positioned with respect to the base, wherein the at least one sensor is of a type selected from the group consisting of: capacitance, force and light; and
   electronics connected operably to the at least one sensor, the electronics receiving a signal from the at least on sensor and configured to process the signal to look for the pinched seam.

13. The open seal check system of claim 12, wherein the base is at least one of: (i) part of a medical fluid heater or a supportive apparatus; (ii) angled; (iii) vertically disposed; and (iv) configured to contact and sense a plurality of multi-chamber supply containers.

14. The open seal check system of claim 12, wherein the seal creates at least two fluid chambers in the container, the electronics configured to determine a difference between signals from a plurality of sensors residing beneath the fluid chambers and at least one signal from at least one sensor residing beneath the pinched seam of the elongated seal.

15. The open seal check system of claim 12, wherein the electronics are further configured to determine at least one of (i) a container closed condition if the pinched seam is sensed;

(ii) a container opened condition if the pinched seam is not sensed; and (iii) a no container present condition.

16. The open seal check system of claim 12, wherein the at least one sensor is elongated and oriented in a same direction as the elongated seal.

17. The open seal check system of claim 12, wherein the at least on sensor is flat to improve an amount of surface area of the container that contacts the base.

18. An open seal check system for a multi-chamber supply container having at least one elongated seal creating a pinched seam along the seal, the system comprising:

a base contacting the multi-chamber container;

at least one sensor positioned with respect to the base, wherein the at least one sensor is flat to improve an amount of surface area of the container that contacts the base; and electronics connected operably to the at least one sensor, the electronics receiving a signal from the at least on sensor and configured to process the signal to look for the pinched seam.

* * * * *